(12) United States Patent
Ferrigno

(10) Patent No.: US 6,303,156 B1
(45) Date of Patent: Oct. 16, 2001

(54) NONINVASIVE METHOD FOR INCREASING OR DECREASING THE BODY TEMPERATURE OF A PATIENT

(75) Inventor: Massimo Ferrigno, Brookline, MA (US)

(73) Assignee: The Brigham and Women's Hospital Inc., Boston, MA (US)

( * ) Notice: Subject to any disclaimer, the term of this patent is extended or adjusted under 35 U.S.C. 154(b) by 0 days.

(21) Appl. No.: 09/337,506

(22) Filed: Jun. 22, 1999

Related U.S. Application Data

(60) Provisional application No. 60/090,521, filed on Jun. 24, 1998, now abandoned.

(51) Int. Cl.[7] .......................... A61K 33/16; A61K 33/00; A61K 33/04; A61M 16/12
(52) U.S. Cl. .......................... 424/673; 424/600; 424/703; 514/816; 514/953; 514/958; 514/959; 252/372; 128/203.16; 128/203.26; 128/204.15; 128/204.17; 128/898; 604/23; 604/500; 604/503; 604/514
(58) Field of Search ..................................... 424/673, 703; 514/953; 252/372; 128/204.15, 204.17; 604/23

(56) References Cited

FOREIGN PATENT DOCUMENTS

861672 * 9/1998 (EP) .

OTHER PUBLICATIONS

Ingenito, et al., "Dissociation of Temperature–Gradient and Evaporative Heat Loss during Cold Gas Hyperventilation in Cold–Induced Asthma," *Am. Rev. Respir. Dis.* 138:540–546 (1988).
International Search Report for PCT/US99/13878 (1999).
Beran, et al., "Hypothermia and Rewarming Induced by Surface and He–$O_2$ Inhalate Temperature Control,"*J. App. Physiol.* 39:337–340 (1975).

* cited by examiner

Primary Examiner—John Pak
(74) Attorney, Agent, or Firm—Michael A. Sanzo; Pillsbury Winthrop LLP

(57) ABSTRACT

The present invention is directed to a method for changing the body temperature of a patient by having them hyperventilate a gas mixture containing sulfur hexafluoride and oxygen. The method may be applied to cool patients in any clinical situation where induced hypothermia is desirable or to rapidly rewarm hypothermic patients. The invention also includes the gas mixtures used in the method.

15 Claims, No Drawings

NONINVASIVE METHOD FOR INCREASING OR DECREASING THE BODY TEMPERATURE OF A PATIENT

CROSS REFERENCE TO RELATED APPLICATIONS

The present application claims the benefit of U.S. provisional application No. 60/090,521, filed on Jun. 24, 1998 (now abandoned).

FIELD OF THE INVENTION

The present invention is directed to noninvasive methods for rapidly changing the body temperature of a patient. This is accomplished by having the patient hyperventilate a gaseous mixture containing sulfur hexafluoride and oxygen. The invention also includes the compositions used in these methods.

BACKGROUND OF THE INVENTION

Patients undergoing operations that require low blood flow or circulatory arrest often must have their body temperature lowered prior to surgery in order to help protect the heart and brain. In particular, hypothermia has been induced in patients undergoing cardiac surgery and operations for cerebral aneurysms. More recently, the lowering of body temperature has been used as a technique for protecting the brain in head trauma patients and there are indications that this procedure may be useful in treating patients for hemorrhagic shock. Unfortunately, there is, at present, no reliable noninvasive method for rapidly lowering a patient's body temperature. The present invention addresses this problem and discloses a method that can be used for rapidly inducing hypothermia or, alternatively, for rapidly warming a hypothermic patient.

SUMMARY OF THE INVENTION

The present invention is based upon the concept that respiratory heat exchange can be used to rapidly change a patient's body temperature. The method requires nothing more than standard hospital equipment such as a ventilator and a means for heating or cooling gases prior to administration to a patient.

In its first aspect, the invention is directed to a method for reducing the body temperature of a patient by administering a gas mixture comprising a combination of sulfur hexafluoride and oxygen. In order to increase the rate of heat exchange, the gas mixture is administered while the patient hyperventilates, either spontaneously or as the result of mechanical ventilation. The mixture being administered must be below the body temperature of the patient and administration is continued until the patient's temperature is reduced to the desired level. Typically, the sulfur hexafluoride will be present at a concentration of between 20 and 80%, with about an 80/20 ratio of sulfur hexafluoride to oxygen being preferred. Unless otherwise indicated, percentages referred to herein indicate a mole percentage. It is also generally preferred that the pressure of carbon dioxide in the patient's arterial blood be maintained within the normal range during gas administration. A reduction in body temperature may be facilitated by maintaining the water vapor content of the gas mixture at low levels, preferably below 10%.

The method discussed above can, alternatively, be used for increasing the body temperature of a patient. The same mixture of sulfur hexafluoride and oxygen is administered but, rather than being cooled prior to administration, it is heated to a temperature above that of the patient. Again, administration of the mixture is maintained until the desired body temperature of the patient is achieved. As with the procedure described above, sodium hexafluoride should be maintained at a concentration of between 20 and 80%, with an 80/20 ratio of sodium hexafluoride to oxygen being preferred. A patient's arterial blood carbon dioxide pressure may be maintained within the normal range during this procedure. In order to further promote an increase in body temperature, the water vapor content of the gas mixture administered to a patient may be maintained at levels of greater than 20 or 40%.

The invention also encompasses the compositions for rapidly changing a patient's body temperature used in the methods described above. Thus, the invention includes mixtures of sulfur hexafluoride and oxygen, typically with the sulfur hexafluoride present at a concentration of 20–80%. Preferably, the composition should have about 80% sulfur hexafluoride. The most desirable concentration of water vapor will depend upon the intended use of the composition. In cases where the composition will be used for lowering the body temperature of a patient, water vapor should, preferably, be present at a concentration of less than 10%. Compositions that will be used to warm a patient should have a concentration of water vapor of greater than 20% and, more preferably, of greater than 40%.

DETAILED DESCRIPTION OF THE INVENTION

The purpose of the present invention is to provide a simple, noninvasive method for rapidly changing the body temperature of a patient. This is accomplished by the patient hyperventilating a breathing mixture containing sulfur hexafluoride and oxygen.

The method is based upon the fact that the convective component of respiratory heat exchange is directly proportional to the minute ventilation, the density of the breathing mixture (gas) and its specific heat, and the difference in temperature between exhaled and inhaled gas. Thus, respiratory heat exchange is maximized by:

1) Increasing minute ventilation: This can be achieved by asking the patient to increase his/her tidal volumes and respiratory rate and/or by using a standard operating room or ICU ventilator in an intubated patient. The patient may be asked to hyperventilate spontaneously prior to being sedated and intubated to achieve faster rates of cooling or rewarming. If eucapnia (also known as isocapnia) is desired, carbon dioxide can be added to the breathing mixture as guided by either end-tidal or arterial pressures of carbon dioxide in the patient.

2) Increasing the density of the gas (breathing mixture): The higher the concentration of sulfur hexafluoride in the mixture, the higher the resulting gas density.

3) Increasing the specific heat of the breathing mixture: This may be accomplished by adding another gas which has a high specific heat to the mixture.

4) Increasing the difference in temperature between exhaled and inhaled gas: In order to cool a patient, the breathing mixture to be inhaled must be cooled below the patient's body temperature; the colder the inhaled breathing gas, the higher the resulting respiratory heat loss. In order to warm a patient, the breathing mixture to be inhaled will be warmed; the warmer the inhaled breathing gas, the higher the resulting respiratory heat gain.

In addition, the content of water vapor in the breathing mixture to be inhaled can be changed to improve the efficiency of the method. For example, the content of water vapor can be decreased (e.g., down to zero) if the patient needs to be cooled; the drier the breathing mixture, the higher the evaporative heat loss. Alternatively, the content of water vapor can be increased (up to saturation) if the patient needs to be rewarmed. This will have the effect of minimizing evaporative heat loss.

In a preferred method, patients are heated or warmed using eucapnic hyperventilation with about an 80/20 sulfur hexafluoride-oxygen mixture. To cool a patient, hyperventilation is performed with a gas mixture to which $CO_2$ is added to maintain isocapnia. The gas mixture is delivered dry and at subfreezing temperature through an endotracheal tube of the type routinely used in operations. To rewarm a patient, hyperventilation is performed with a humidified and warmed gas mixture.

The gas mixtures administered to patients may be mixed in a reservoir and then delivered to patients by means of a ventilator of the sort commonly available in hospitals. In procedures designed to lower body temperature, the gas mixture may be forced through a desiccator to remove water vapor and through a heat exchanger to lower its temperature (see e.g., Beran, et al., *J. App. Physiol.* 39:337–340 (1975)). In procedures designed to increase body temperature, gases from a mixing reservoir may be delivered using a ventilator, humidified, and warmed by a standard electrically operated heater/humidifier system. As with cooling, rewarming will be accomplished using a gas mixture of sulfur hexafluoride and oxygen. These procedures are merely illustrative and the invention is compatible with any other method for heating or cooling gas mixtures and for effectively delivering them to a patient.

The simplest way for achieving hyperventilation will be by means of the voluntary cooperation of a patient immediately prior to their being anesthetized. In patients who are unconscious or anesthetized, hyperventilation may be induced using a standard operating room or ICU ventilator. The monitoring of a patient's temperature and arterial blood gas values may be accomplished using procedures that are routine in the art.

The present methods will typically be used for cooling patients prior to cardiac or neurosurgery. They may also be used to rapidly lower the body temperature of patients suffering from hemorrhagic shock or in an emergency room setting for rapidly rewarming hypothermic patients. In general, the procedures may be performed on all patients in whom core temperature changes are desired, with the possible exception of those with asthma. In these patients, there is a risk of inducing bronchospasm and the risk/benefit ratio of using the techniques will need to be considered on a case by case basis.

What is claimed is:

1. A method of reducing the body temperature of a patient for any clinical condition in which a reductor in body temperature is desirable, comprising:
   a) administering a gas mixture to said patient by hyperventilation, wherein:
      i) said gas mixture comprises a combination of sulfur hexafluoride and oxygen;
      ii) said gas mixture is administered at a temperature below the body temperature of said patient; and
   b) maintaining the administration of the gas mixture of step a) until said patient's body temperature is reduced.

2. The method of claim 1, wherein said sulfur hexafluoride is present at a concentration of 20–80 mole percent.

3. The method of claim 1, wherein said sulfur hexafluoride is present at a concentration of about 80 mole percent.

4. The method of claim 1, wherein the concentration of carbon dioxide in said patient's blood is maintained in the normal range.

5. The method of claim 1, wherein the water vapor content of said gas mixture is less than 10 mole percent.

6. The method of claim 1, wherein said patient is cooled in preparation for or during surgery.

7. The method of claim 6, wherein said surgery is cardiac or neurosurgery.

8. The method of claim 1, wherein said patient is cooled as a treatment for hemorrhagic shock.

9. A method of increasing the body temperature of a patient for any clinical condition in which an increase in body temperature is desirable, comprising:
   a) administering a gas mixture to said patient by hyperventilation, wherein:
      i) said gas mixture comprises a combination of sulfur hexafluoride and oxygen;
      ii) said gas mixture is administered at a temperature above the body temperature of said patient; and
   b) maintaining the administration of the gas mixture of step a) until said patient's body temperature is increased.

10. The method of claim 9, wherein said sulfur hexafluoride is present at a concentration of 20–80 mole percent.

11. The method of claim 9, wherein said sulfur hexafluoride is present at a concentration of about 80 mole percent.

12. The method of claim 9, wherein the pressure of carbon dioxide in said patient's arterial blood is maintained in the normal range.

13. The method of claim 9, wherein the water vapor content of said gas mixture is greater than 20 mole percent.

14. The method of claim 9, wherein the water vapor content of said gas mixture is greater than 40 mole percent.

15. The method of claim 9, wherein the body temperature of said patient is increased as a treatment for hypothermia.

* * * * *